(12) United States Patent
Ferguson et al.

(10) Patent No.: US 9,140,673 B2
(45) Date of Patent: Sep. 22, 2015

(54) METHOD FOR FABRICATING COMPOSITE POROSITY STANDARDS

(71) Applicant: The Boeing Company, Chicago, IL (US)

(72) Inventors: Kathy L. Ferguson, Woodinville, WA (US); John F. Spalding, Renton, WA (US)

(73) Assignee: The Boeing Company, Chicago, IL (US)

( * ) Notice: Subject to any disclaimer, the term of this patent is extended or adjusted under 35 U.S.C. 154(b) by 275 days.

(21) Appl. No.: 13/902,891

(22) Filed: May 27, 2013

(65) Prior Publication Data

US 2014/0346405 A1 Nov. 27, 2014

(51) Int. Cl.
*G01N 29/30* (2006.01)
*G01N 15/08* (2006.01)
*G01N 1/28* (2006.01)

(52) U.S. Cl.
CPC .............. *G01N 29/30* (2013.01); *G01N 15/088* (2013.01); *G01N 2001/2893* (2013.01); *Y10T 436/10* (2015.01); *Y10T 436/109163* (2015.01)

(58) Field of Classification Search
CPC ..................... G01N 15/088; G01N 2001/2893; G01N 29/30; Y10T 436/10; Y10T 436/109163
USPC ............... 436/8, 19, 183; 73/1.01, 1.03, 1.82, 73/1.86; 252/408.1; 156/242
See application file for complete search history.

(56) References Cited

U.S. PATENT DOCUMENTS

| | | | |
|---|---|---|---|
| 4,982,086 A | 1/1991 | Withjack | |
| 7,010,980 B2 | 3/2006 | Meier | |
| 7,357,014 B2 | 4/2008 | Vaccaro et al. | |
| 7,617,714 B2 | 11/2009 | Engelbart et al. | |
| 7,617,715 B2 | 11/2009 | Georgeson et al. | |
| 7,694,546 B2 | 4/2010 | Engelbart et al. | |
| 7,752,882 B2 * | 7/2010 | Vaccaro et al. | 73/1.86 |
| 7,770,457 B2 | 8/2010 | Engelbart et al. | |
| 8,642,164 B2 * | 2/2014 | Watson et al. | 428/212 |
| 9,002,088 B2 * | 4/2015 | Ferguson | 382/131 |
| 2007/0095141 A1 | 5/2007 | Puckett | |
| 2007/0101815 A1 | 5/2007 | Kollgaard et al. | |
| 2010/0258235 A1 * | 10/2010 | Whitworth et al. | 156/94 |
| 2012/0138609 A1 * | 6/2012 | Gerken et al. | 220/62.19 |
| 2014/0072197 A1 | 3/2014 | Ferguson | |

FOREIGN PATENT DOCUMENTS

| | | |
|---|---|---|
| EP | 2 019 315 | 1/2009 |
| EP | 2 706 345 | 3/2014 |

OTHER PUBLICATIONS

International Search Report and Written Opinion, PCT/US2014/036559 (2014).
Grove et al., "jPOR: An ImageJ macro to quantify total optical porosity from blue-stained thin sections," *Computer & Geosciences*, vol. 37, No. 11 (2011).

* cited by examiner

*Primary Examiner* — Maureen Wallenhorst
(74) *Attorney, Agent, or Firm* — Walters & Wasylyna LLC (57) ABSTRACT

A method for fabricating composite porosity standards may include the steps of providing a plurality of uncured composite coupons, each uncured composite coupon being formed from a composite material, providing a plurality of curing processes, selecting a curing process for each of the uncured composite coupons, curing each uncured composite coupon in accordance with a selected curing process to form a plurality of cured composite coupons, each cured composite coupon being formed from the composite material and having a percent porosity, measuring the percent porosity of each cured composite coupon, and correlating each measured percent porosity of a plurality of measure percent porosities to a corresponding cured composite coupon of the plurality of cured composite coupons to form a plurality of porosity standards.

24 Claims, 7 Drawing Sheets

| MATERIAL | CURING PROCESS | % POROSITY |
|---|---|---|
| BMS 8-340 | S-AC | 0.3% - 0.4% |
| BMS 8-340 | LE-AC | 0.6% - 1.3% |
| BMS 8-340 | LE-HB-HV | 1.1% - 1.4% |
| BMS 8-340 | S-HB-HV | 1.7% - 2.1% |
| BMS 8-340 | LE-HB-SV | 2.4% - 2.6% |
| BMS 8-340 | S-OC-SV | 2.8% - 4.3% |

FIG. 4

| MATERIAL | CURING PROCESS | % POROSITY |
|---|---|---|
| EA 9390 | S-AC-DVD | 0.1% - 0.2% |
| EA 9390 | S-HB-DVD | 0.5% - 0.6% |
| EA 9390 | S-OC-SV | 8.3% - 13.6% |

METHOD FOR FABRICATING COMPOSITE POROSITY STANDARDS

FIELD

The present disclosure is generally related to nondestructive reference standards and, more particularly, to a method for fabricating composite porosity reference standards for nondestructive testing.

BACKGROUND

As the use of composite materials increases, the development of advanced nondestructive testing (NDT) techniques for composite materials is in demand. Ultrasonic quantitative NDT techniques for composite materials may provide good information on manufacturing quality, material strength and perhaps useful lifetime. Additionally, the effects of porosity in composite laminates on ultrasonic attenuation can be used in gauging the porosity content in composite material.

Ultrasonic NDT techniques require a porosity reference standard to calibrate the measurements for a composite component provided by the ultrasonic testing equipment. Unfortunately, the process of fabricating porosity reference standards is complicated, time consuming, and very expensive. Typically this process requires large numbers of composite coupons to be fabricated and many testing sites or samples to be taken for porosity measurements. Selection of testing sites is essentially random, which requires iterations of coupon fabrication and porosity measurements to form reference standards representing a range of percent porosities.

Additionally, porosity standards fabricated using artificial materials to simulate porosity may not provide accurate attenuation measurements when compared to natural porosity occurring in a composite component.

Accordingly, those skilled in the art continue with research and development efforts in the field of fabrication of reference porosity standards.

SUMMARY

In one aspect, the disclosed method for fabricating a composite porosity standard may include the steps of: (1) selecting a curing process for an uncured composite coupon; (2) curing said uncured composite coupon in accordance with said selected curing process to form a cured composite coupon; (3) measuring a percent porosity of said cured composite coupon; and (4) correlating said measured percent porosity to said cured composite coupon to form a porosity standard.

In one aspect, the disclosed method for fabricating composite porosity standards may include the steps of: (1) providing a plurality of uncured composite coupons, each uncured composite coupon of the plurality of uncured composite coupons including a composite material, (2) providing a plurality of curing processes, (3) selecting a curing process of the plurality of curing processes for each of the uncured composite coupons, (4) curing each uncured composite coupon of the plurality of composite coupons in accordance with a selected curing process of the plurality of curing processes to form a plurality of cured composite coupons, each cured composite coupon of the plurality of cured composite coupons including the composite material having a percent porosity, (5) measuring the percent porosity of each cured composite coupon of the plurality of cured composite coupons, and (6) correlating each measured percent porosity of a plurality of measure percent porosities to a corresponding cured composite coupon of the plurality of cured composite coupons to form a plurality of porosity standards.

In another aspect, the disclosed method for fabricating composite porosity standards may include the steps of: (1) providing a plurality of uncured composite coupons, each uncured composite coupon of the plurality of uncured composite coupons including a composite material, (2) providing a plurality of curing processes, (3) selecting a curing process of the plurality of curing processes for each of the uncured composite coupons, (4) curing each uncured composite coupon of the plurality of composite coupons in accordance with a selected curing process of the plurality of curing processes to form a plurality of cured composite coupons, each cured composite coupon of the plurality of cured composite coupons including the composite material having a percent porosity, (5) measuring the percent porosity of each cured composite coupon of the plurality of cured composite coupons, (6) correlating each measured percent porosity of a plurality of measured percent porosities to a corresponding cured composite coupon of the plurality of cured composite coupons to form a plurality of porosity standards, (7) correlating each measured percent porosity of the plurality of measure percent porosities to a corresponding selected curing process of the plurality of curing processes, (8) ranking the plurality of curing processes based on a correlated measured percent porosity of the selected curing process, and (9) creating a porosity tree representing the plurality of curing processes as ranked from a lowest correlated measured percent porosity to a highest correlated measured percent porosity.

In another aspect, the disclosed method for fabricating composite porosity standards may include the steps of: (1) providing a plurality of uncured composite coupons, each uncured composite coupon of the plurality of uncured composite coupons including a composite material, (2) providing a plurality of curing processes, (3) selecting a curing process of the plurality of curing processes for each of the uncured composite coupons, (4) curing each uncured composite coupon of the plurality of composite coupons in accordance with a selected curing process of the plurality of curing processes to form a plurality of cured composite coupons, each cured composite coupon of the plurality of cured composite coupons including the composite material having a percent porosity, (5) measuring the percent porosity of each cured composite coupon of the plurality of cured composite coupons, (6) correlating each measured percent porosity of a plurality of measured percent porosities to a corresponding cured composite coupon of the plurality of cured composite coupons to form a plurality of porosity standards, (7) providing a composite component including a composite material, wherein the composite material of the plurality of cured composite coupons is substantially the same as the composite material of at least a portion of the composite component, (8) evaluating an attenuation of the composite component, (9) evaluating an attenuation of at least one porosity standard of the plurality of porosity standards, (10) comparing attenuation measurements of the composite component to the at least one porosity standard, and (11) validating a percent porosity of the composite component.

Also disclosed is an aspect of a composite porosity reference standard, the disclosed composite porosity reference standard may include a cured composite coupon including a composite material having a percent porosity, the percent porosity being a result of a selected curing process on the composite material, and a measured percent porosity of the cured composite coupon.

Other aspects of the disclosed method for fabricating composite porosity standards will become apparent from the following detailed description, the accompanying drawings and the appended claims.

DETAILED DESCRIPTION

The following detailed description refers to the accompanying drawings, which illustrate specific aspects of the disclosure. Other aspects having different structures and operations do not depart from the scope of the present disclosure. Like reference numerals may refer to the same element or component in the different drawings.

Figure 1:
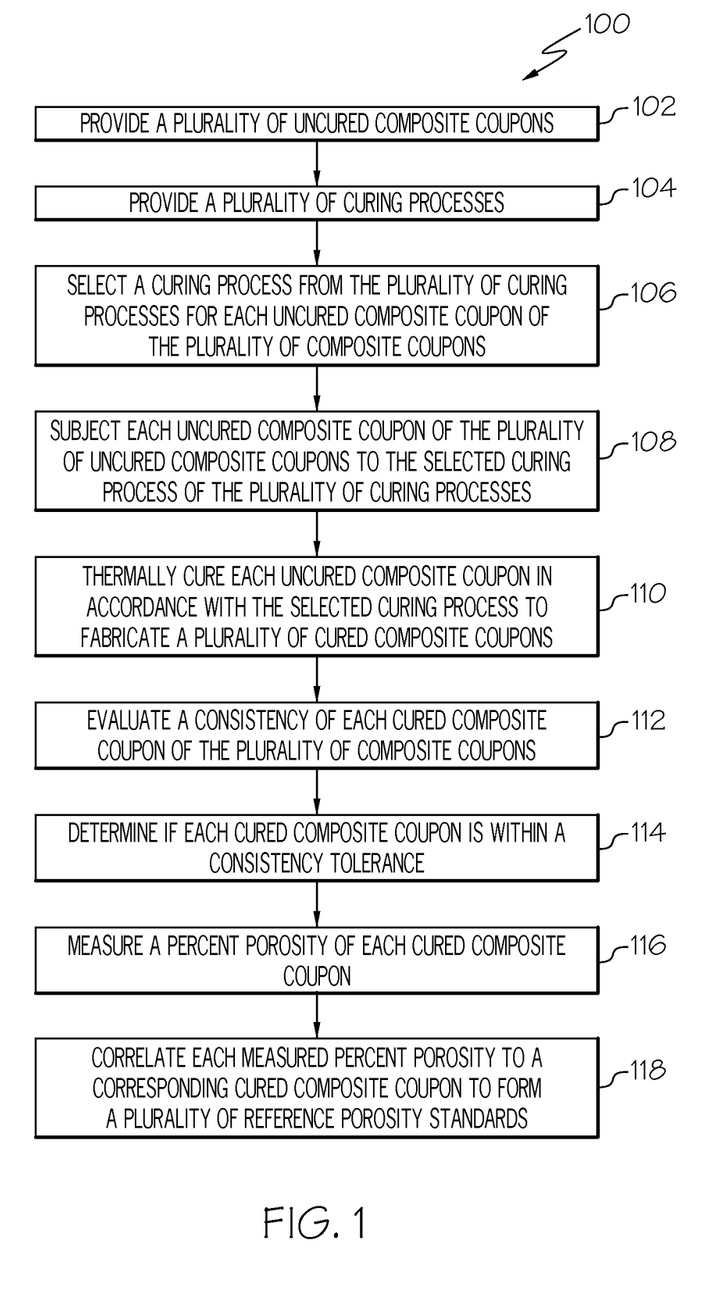
FIG. 1 is a flow diagram of an aspect of the disclosed method for fabricating composite porosity reference standards.
Figure 2:
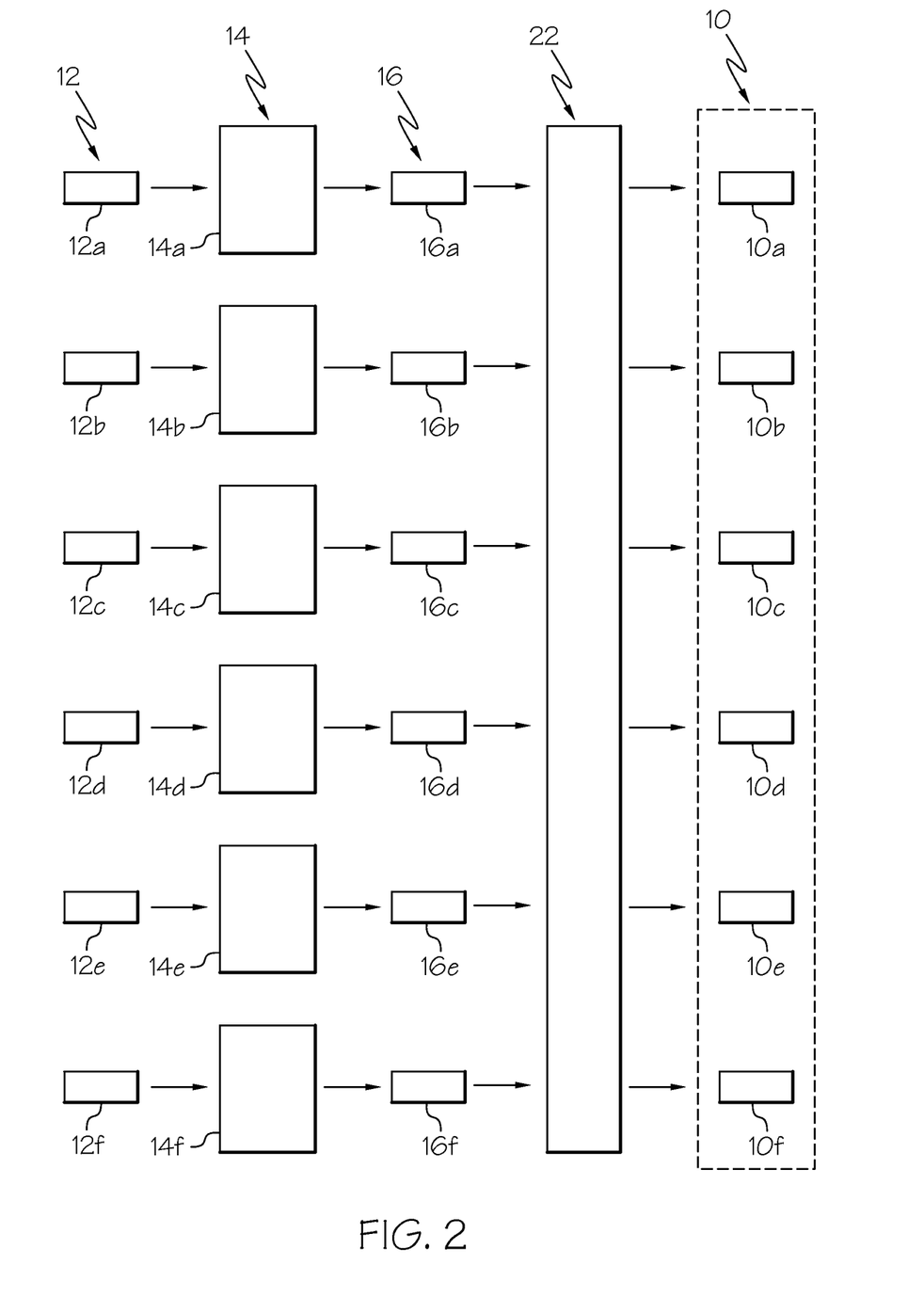
FIG. 2 is a block diagram of an aspect of a system for implementing one or more operations of the disclosed method for fabricating composite porosity reference standards.

Referring to FIGS. 1 and 2, disclosed is one aspect of a method, generally designated 100, for fabricating nondestructive testing (NDT) reference porosity standards for a composite material. Each porosity standard 10a-10f of a plurality of porosity standards 10 may include a cured composite coupon 16 having a measured volumetric porosity associated with the cured composite coupon 16. A set of porosity standards 10 may be used to (1) calibrate ultrasonic testing equipment for measuring and validating porosity of a composite component (e.g., part) and/or (2) create a porosity tree of expected volumetric porosity of a composite material with respect to selected curing processes.

Figure 3:
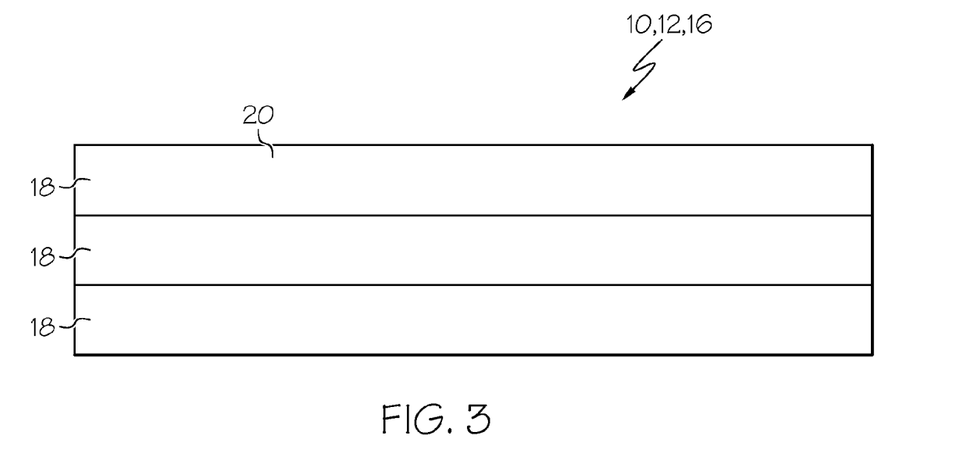
FIG. 3 is a side elevational view of a composite coupon.

As shown at block 102, the method 100 may include the step of providing a plurality of uncured composite coupons 12. Each of the uncured composite coupons 12 may include a selected composite material 20 (FIG. 3). The composite material 20 (e.g., material class, grade, and type and the number of plies) forming the uncured coupon 12 may be substantially the same as the composite material (e.g., material class, grade, and type and the number of plies) forming the composite component for which porosity is to be measured and validated.

Referring to FIG. 3, the composite material 20 may include a reinforcement material and a matrix material. The reinforcement material may be any material suitable to reinforce (e.g., strengthen or stiffen) a composite structure (e.g., part). For example, the reinforcement material may include, but is not limited to, particles, continuous or discontinuous fibers (e.g., carbon, boron, glass, or aramid), mats, and fabrics (e.g., woven, stitched, or braided). The matrix material may be any material suitable to bind the reinforcing material and transfer stress between reinforcing materials. For example, the matrix material may include, but is not limited to, a thermoset resin (e.g., polyesters, epoxies, vinyl esters, or phenolics) and a thermoplastic resin. One skilled in the art can appreciate additional constituent materials, fillers, modifiers, or additives may also be used to form the uncured composite coupon 12 or the composite component, such as toughening agents, interlayer-tougheners, catalysts, release agents, or the like.

The composite material 20 (e.g., forming the uncured composite coupon 12 (FIG. 2), the cured composite coupon 16 and the porosity standard 10) may include at least two plies or lamina 18 (three are shown in FIG. 3). Each ply 18 may include reinforcing material and matrix material substantially the same as the composite component for which porosity is to be measured and validated. The uncured composite coupon 12 may include a unidirectional reinforcing material (e.g., fibers) or a bidirectional reinforcing material (e.g., woven fabric). The uncured composite coupon 12 may include a plurality of stacked plies 18 forming a laminate composite body. For example, the uncured composite coupon 12 may include between 2 and 100 plies. As another example, the uncured composite coupon may include between 5 and 50 plies. As another example, the uncured composite coupon may include between 10 and 30 plies. As still another example, the uncured composite coupon may include 20 plies.

The total number of plies 18 forming the uncured composite coupon 12 and, thus, the cured composite coupons 16 and porosity standards 10 (FIG. 2), may be substantially the same as the total number of plies 18 forming the composite component for which porosity is to be measured and validated. For example, the cured composite coupon 16 may include substantially the same number of plies 18 as a manufactured composite part. Substantially the same number of plies 18 may include exactly the same number of plies 18 as the number of plies of the composite component or a number of plies 18 within an acceptable range (e.g., within five (5) plies) representing the number of plies of the composite component.

As another example, the cured composite coupon 16 may include a number of plies 18 representative of the minimum number of plies used in a one-dimensional or two-dimensional repair (e.g., patch) of a composite part. As still another example, the cured composite coupon 16 may include a number of plies 18 representative of the maximum number of plies used in a one-dimensional or two-dimensional repair of a composite part. As still another example, the cured composite coupon 16 may include variations in the number of plies 18 used, such as a first number of plies 18 forming a first portion of the coupon 16 and a second number of plies 18 forming a second portion of the coupon 16, where the first number of plies 18 is different from the second number of plies 18.

In one example implementation, the composite material 20 (e.g., forming the uncured composite coupon 12) may be a prepreg material (e.g., composite) where each ply may include reinforcing material that is pre-impregnated with matrix material substantially the same as the composite component for which porosity is to be measured and validated. The prepreg composite may be fabricated in accordance with any known process. In one specific non-limiting example, the uncured composite coupon 12 may be formed using BMS 8-340 prepreg fabric. Thus, in an example implementation, the porosity standards 10 may be formed using substantially the same number of plies of BMS 8-340 prepreg fabric as the number of plies of BMS 8-340 used to form the composite component.

In another example implementation, the composite material 20 (e.g., forming the uncured composite coupon 12) may be a wet lay-up composite where matrix material is transferred to each ply of reinforcing material substantially the same as the composite component for which porosity is to be measured and validated. The wet lay-up composite may be fabricated in accordance with any known process. In another specific non-limiting example, the uncured composite coupon 12 may be formed using EA 9390 wet lay-up material including BMS 9-17 fabric and BMS 8-301 resin. Thus, in an example implementation, the porosity standards 10 may be formed using substantially the same number of plies of EA 9390 as the number of plies of EA 9390 used to form the composite component.

However, one skilled in the art can appreciate that any prepreg or wet lay-up composite material may be used to form the uncured composite coupon 12 and/or the composite component for which porosity is to be measured and validated, without limitation.

Referring again to FIGS. 1 and 2, as shown at block 104, the method 100 may include providing a plurality of curing processes 14. Each curing process 14 of the plurality of curing processes 14 may be different. Each curing process 14 of the plurality of curing processes 14 may include at least one associated particular curing parameter (e.g., time, temperature, and/or pressure). The curing parameters of each curing process 14 may be different.

Each curing processes 14 may be any thermal cure cycle suitable to expose the composite material 20 (FIG. 3) to elevated temperatures and/or pressures for a predetermined length of time. The elevated temperatures applied during the curing process 14 may provide the heat required for initiating and maintaining chemical reactions in the matrix material (e.g., resin), which cause desired changes in molecular structure of the matrix material. The applied pressure may provide the force needed to squeeze excess matrix material (e.g., resin) out of the reinforcing material (e.g., fabric), to consolidate individual plies 18, and to compress vapor bubbles.

For example, the curing process 14 may include, but is not limited to, an oven cure process, an autoclave cure process, and a heat blanket cure process. The curing process 14 may include, but is not limited to, a standard vacuum (e.g., about 22 to 26 inches mercury (in Hg)) and a high vacuum (e.g., about 27 to about 30 in Hg). The curing process may also include, but is not limited to, a vacuum bag cure process and a double vacuum debulk cure process. As used herein, the term "double vacuum debulk" means a process in which a stack of plies may be subjected to vacuum and mild heating without being compacted by atmospheric pressure. The purpose of the double vacuum debulk process is to minimize porosity in the plies by drawing air and other gases from between the plies while they are in an uncompacted state.

The curing process 14 may be a standard process where temperature increases due to exothermic reaction of the matrix material may be ignored. Alternatively, the curing process 14 may be a low exothermic process where temperature increases due to exothermic reaction of the matrix material may be controlled. For example, a low exothermic curing process may include a relatively slow temperature ramp up and a hold period at a designated temperature (e.g., 212° F.) to allow the matrix material sufficient time to reach cure temperature via exothermic reactions. As another example, a standard curing process may have a relatively faster temperature ramp up (e.g., than a low exothermic curing process) and may not include a hold period at a designated temperature (e.g., 212° F.), such that the matrix material may overshoot the maximum curing temperature (e.g., by as much as 100° F.) due to exothermic reactions. However, the curing process 14 may be any other suitable thermal cure process having any curing parameters, without limitation.

Referring still to FIGS. 1 and 2, as shown at block 106, the method may include the step of selecting a curing process 14a-14f from the plurality of provided curing processes 14 for each uncured composite coupon 12a-12f of the plurality of uncured composite coupons 12.

As shown at block 108, each uncured composite coupon 12a-12f of the plurality of uncured composite coupons 12 may be subjected to the selected curing process 14a-14f of the plurality of curing processes 14.

As shown at block 110, the plurality of composite coupons 12 may be thermally cured to form a plurality of cured composites 16. Each uncured composite coupon 12a-12f may be cured by an associated curing process 14a-14f of the plurality of selected curing processes 14. Each curing process 14a-14f may cure the uncured composite coupon 12a-12f to form a cured composite coupon 16a-16f having a relatively consistent volumetric porosity.

For example, referring to FIG. 2, a first uncured composite coupon 12a may be subjected to a first curing process 14a to form a first cured composite coupon 16a having a first percent porosity. A second uncured composite coupon 12b may be subjected to a second curing process 14b to form a second cured composite coupon 16b having a second percent porosity. A third uncured composite coupon 12c may be subjected to a third curing process 14c to form a third cured composite coupon 16c having a third percent porosity. A fourth uncured composite coupon 12d may be subjected to a fourth curing process 14d to form a fourth cured composite coupon 16d having a fourth percent porosity. A fifth uncured composite coupon 12e may be subjected to a fifth curing process 14e to form a fifth cured composite coupon 16e having a fifth percent porosity. A sixth uncured composite coupon 12f may be subjected to a sixth curing process 14f to form a sixth cured composite coupon 16f having a sixth percent porosity.

As expressed above, each cured composite coupon 16a-16f of the plurality of cured composite coupons 16 may include substantially the same composite material 20 (FIG. 3) as one another and substantially the same composite material as the composite component for which porosity is to be measured and validated.

One skilled in the art can appreciate that any number of uncured composite coupons 12 may be subjected to any number of different curing processes 14 to form any number of cured composite coupons 16 having a range of porosities. The differences in porosity of the cured composite coupons 16 may depend on the type of curing process 14, the curing parameters, and the composite materials used.

Each uncured composite coupon 12 and, thus, each cured composite coupon 16 may be of any suitable shape and size. The size of the uncured composite coupon 12 may be selected or configured to optimize consistency of porosity throughout the cured composite coupon 16 and thus, the reference porosity standards 10 taken from the cured composite coupon 16. An uncured composite coupon 12 being relatively small in size (e.g., no greater that twelve-inches by twelve-inches) may prevent large variations in porosity throughout the cured composite coupon 16 following a selected curing process 14 (FIG. 2).

As the thickness (e.g., number of plies 18) of the uncured composite coupon 12 increases (e.g., up to 24 plies), optimizing the size (e.g., length and width) and shape of the uncured composite coupon 12 may be advantageous in achieving consistent porosity throughout the cured composite coupon 16. For example, as the thickness of the uncured composite coupon 12 increases, the size (e.g., length and width) of the uncured composite coupon 12 may be decreased in order to adequately allow off-gases and/or moisture to migrate to the edges and escape during the selected curing process. Additionally, in order to control exothermic reactions of exothermally reactive composite materials (e.g., BMS8-340), a smaller uncured composite coupon 12 may be beneficial.

For example, the cured composite coupon 16 being appropriately sized (e.g., approximately twelve inches by twelve inches) may have substantially consistent porosity (e.g., pore size, pore shape, pore location, and/or pore distribution) across the coupon panel. Consistent porosity across the cured composite coupon 16 may provide reliable and substantially equivalent reference porosity standards 10 (e.g., taken from that cured composite coupon 16) having percent porosities throughout that are consistent with and substantially the same as the measured percent porosity of the cured composite coupon 16, as described below in the method step shown at block 116 of FIG. 1. Whereas, a cured composite coupon being substantially larger in size (e.g., thirty-six inches by thirty-six inches) may have inconsistent porosity (e.g., pore size, pore shape, pore location, and/or pore distribution) across the cured composite panel.

In an example construction, the uncured composite coupon 12 may be a square. In another example construction, the uncured composite coupon 12 may be rectangular. As expressed above, a rectangular uncured composite coupon 12 may be beneficial as the thickness (e.g., number of plies 18) increases due to the off-gases and/or moisture having a shorter pathway to vent or escape from the coupon during the selected curing process 14, thus, improving porosity consistency across the cured composite coupon 16 and/or reducing the overall percent porosity throughout the cured composite coupon 16.

In an example implementation of the first example construction, the uncured composite coupon 12 may be a twelve-inch by twelve-inch square forming a twelve-inch by twelve-inch cured composite coupon 16. The twelve-inch by twelve-inch cured composite coupon 16 (e.g., parent) may be partitioned into a plurality of smaller porosity standards 10, such as four (4) three-inch by three-inch squares of three (3) four-inch by four-inch squares. In an example implementation of the second example construction, the uncured composite coupon 12 may be a twelve-inch by six-inch rectangle forming a rectangular composite coupon 16. However, the uncured composite coupons 12 and the cured composite coupons 16 may include any shape and any dimensions, without limitation.

Referring again to FIGS. 1 and 2, as shown at block 112, the method 100 may include the step of evaluating the consistency of each cured composite coupon 16a-16f of the plurality of cured composite coupons 16. Evaluation of each cured composite coupon 16 may be achieved through any known ultrasonic testing process to determine if the attenuation (e.g., the reduction in amplitude of an ultrasound beam as a function of porosity through the cured composite material 20) is consistent throughout the cured composite coupon 16.

For example, each cured coupon 16 may be evaluated using ultrasound C-Scan to provide a visual representation of the attenuation throughout the cured composite coupon 16 (e.g., image). As another example, each cured composite coupon 16 may be evaluated using ultrasonic A-Scan to provide a numeric representation of the attenuation throughout the cured composite coupon 16 (e.g., decibel loss).

As shown at block 114, upon validation of a consistent attenuation throughout the cured composite coupon 16, a determination may be made whether or not the cured composite coupon 16 meets any required minimum variation standards for use as a porosity reference standard 10. For example, if the evaluated attenuation throughout the cured composite coupon 16 is consistent (e.g., within acceptable consistency tolerances), the percent volumetric porosity of the cured composite coupon 16 may be measured. If the evaluated attenuation throughout the cured composite coupon 16 is inconsistent (e.g., not within acceptable tolerances), the cured composite coupon 16 may be scrapped.

As shown at block 116, the method 100 may include the step of measuring a volumetric percent porosity in each validated cured composite coupon 16 (e.g., within a consistency tolerance) of the plurality of cured composite coupons 16. Measurement of volumetric percent porosity of each cured composite coupon 16 may be achieved through any known measuring process.

As an example, the percent porosity may be measured using Image-J analysis. At least one sample may be taken from each cured composite coupon 16. Each sample may be cut or otherwise removed using any known technique. For example, a pair of small strips (e.g., two-and-a-half-inch by two-inch) may be cut from each cured composite coupon 16. At least one edge of the sample may be polished and an image of the polished surface may be examined using Image-J analysis software to quantify the percent volumetric porosity in the sample. However, any other suitable imaging analysis including, but not limited to, computed tomography (i.e., CT Scan) may be used to measure and quantify the percent porosity of each cured composite coupon 16.

For example, the first cured composite coupon 16a may have a first measured percent porosity. The second cured composite coupon 16b may have a second measured percent porosity. The third cured composite coupon 16c may have a third measured percent porosity. The fourth cured composite coupon 16d may have a fourth measured percent porosity. The fifth cured composite coupon 16e may have a fifth measured percent porosity. The sixth cured composite coupon 16f may have a sixth measured percent porosity. Each of the plurality of cured composite coupons 16 may be evaluated and measured using any suitable testing equipment 22.

As shown at block 118, the plurality of cured composite coupons 16 and the plurality of measured percent porosities may be correlated such that each cured composite coupon 16 may be identified by a corresponding measured percent porosity to form a plurality of reference porosity standards 10. The plurality of porosity standards 10 may represent a range of percent porosities for the composite material 20 used to form the composite coupon 16. The percent porosities may range, for example, from about 0% to about 15%.

As shown in FIG. 2, for example, a first porosity standard 10a may represent a percent porosity of about 0%. The second porosity standard 10b may represent a percent porosity of about 1%. The third porosity standard 10c may represent a percent porosity of about 2%. The fourth porosity standard 10d may represent a percent porosity of about 4%. The fifth porosity standard 10e may represent a percent porosity of about 8%. The sixth porosity standard 10f may represent a percent porosity of about 13%.

Figure 4:
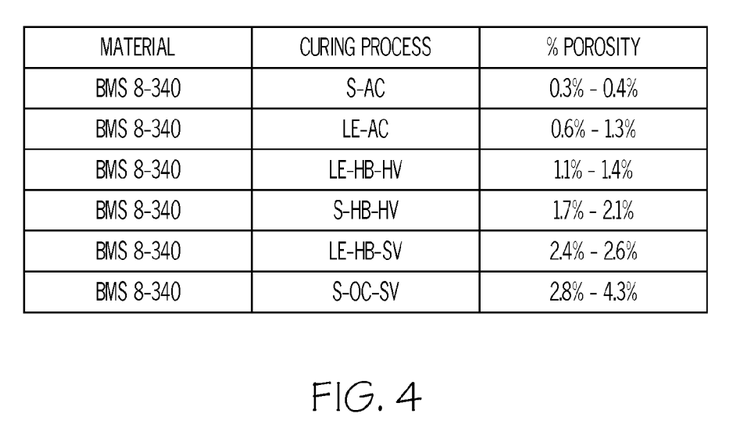
FIG. 4 is an illustration of an example table of different measured percent porosities of a plurality of cured composite coupons.

Referring to FIG. 4, illustrating an example table of different measured percent porosities of a plurality of cured composite coupons subjected to the method steps shown at blocks 104-114 of FIG. 1. More specifically, in accordance with experimental data, a plurality of uncured composite coupons fabricated from between about 18 and 23 plies of BMS 8-340 prepreg fabric were submitted to a variety of curing processes to form a plurality of cured BMS 8-340 composite coupons. The attenuation of each of the cured BMS 8-340 composite coupons was validated and the percent porosity was measured.

A BMS 8-340 composite coupon subjected to a standard autoclave curing process ("S-AC") had a measured percent porosity of between 0.3% and 0.4%. A BMS 8-340 composite coupon subjected to a low exothermic autoclave curing process ("LE-AC") had a measured percent porosity of between 0.6% and 1.3%. A BMS 8-340 composite coupon subjected to a low exothermic heat blanket curing process under high vacuum ("LE-AC-HV") had a measured percent porosity of between 1.1% and 1.4%. A BMS 8-340 composite coupon subjected to a standard heat blanket curing process under high vacuum ("S-AC-HV") had a measured percent porosity of between 1.7% and 2.1%. A BMS 8-340 composite coupon subjected to a low exothermic heat blanket curing process under standard vacuum ("LE-AC-SV") had a measured percent porosity of between 2.4% and 2.6%. A BMS 8-340 composite coupon subjected to a standard oven curing process under standard vacuum ("S-OC-SV") had a measured percent porosity of between 2.8% and 4.3%.

Thus, the experimental method for fabricating porosity standards for BMS 8-340 provided reference porosity standards ranging from 0.3% to 4.3%.

Figure 5:
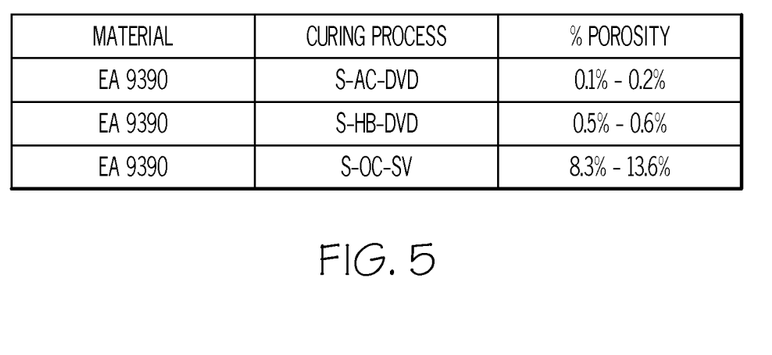
FIG. 5 is an illustration of another example table of different measured percent porosities of a plurality of cured composite coupons.

Referring to FIG. 5, illustrating another example table of different measured percent porosities of a plurality of cured composite coupons subjected to the method steps shown at blocks 104-114 of FIG. 1. More specifically, in accordance with experimental data, a plurality of uncured composite coupons fabricated from between 18 and 23 plies of EA 9390 wet lay-up were submitted to a variety of curing processes to form a plurality of cured EA 9390 composite coupons. The attenuation of each of the cured EA 9390 composite coupons was validated and the percent porosity was measured.

An EA 9390 composite coupon subjected to a standard autoclave curing process under double vacuum debulk ("S-AC-DVD") had a measured percent porosity of between 0.1% and 0.2%. An EA 9390 composite coupon subjected to a standard heat blanket curing process under double vacuum debulk ("S-HB-DVD") had a measured percent porosity of between 0.5% and 0.6%. An EA 9390 composite coupon subjected to a standard oven curing process under standard vacuum ("S-OC-SV") had a measured percent porosity of between 8.3% and 13.6%.

Thus, the experimental method for fabricating porosity standards for EA 9390 provided reference porosity standards ranging from 0.1% to 13.6%.

Figure 6:
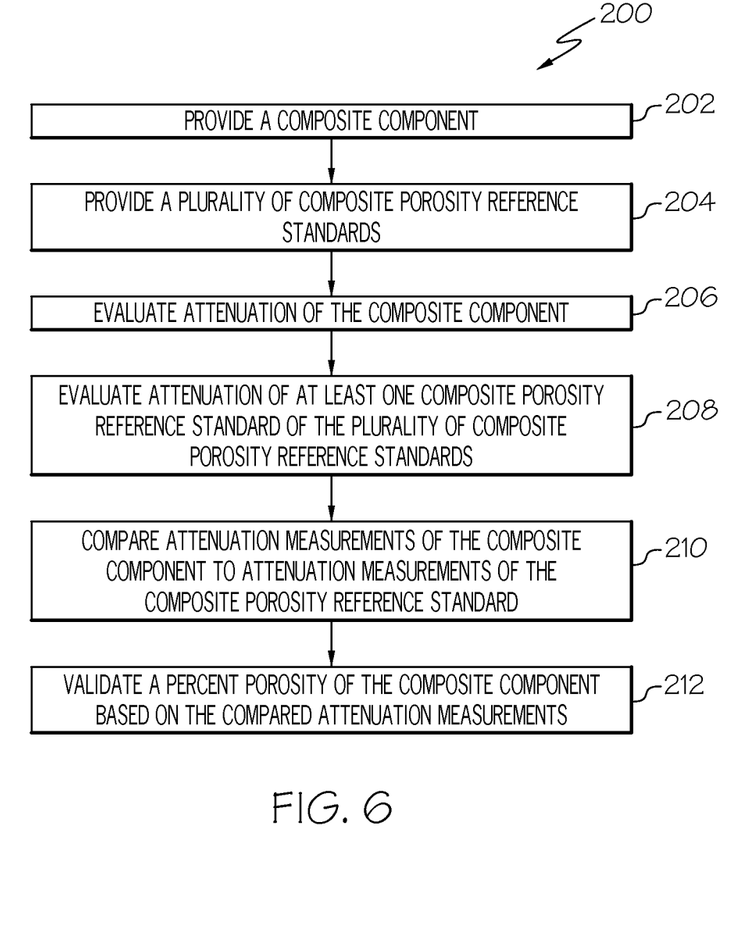
FIG. 6 is flow diagram of an aspect of the disclosed method for validating a percent porosity of a composite component using the disclosed composite porosity reference standards.

Referring to FIG. 6, also disclosed is a method, generally designated 200, for validating a percent porosity of a composite component using the disclosed composite porosity reference standards 10 fabricated in accordance with the method 100 illustrated in FIG. 1. As shown at block 202, a composite component may be provided. The composite component may be formed from a composite material and may have a number of plies.

As shown at block 204, the method 200 may include the step of providing a plurality of reference porosity standards 10 (FIG. 2). Each porosity standard 10 may include a cured composite coupon 16 having a correlated measured percent porosity identifier. As expressed above in accordance with the method 100, each porosity standard 10 may include substantially the same material class, grade, type, and number plies as used in the composite component.

As shown at block 206, the attenuation of the composite component may be evaluated. For example, ultrasonic testing equipment may be used to measure the reduction in amplitude of an ultrasound beam as a function of porosity through the material of the composite component.

As shown at block 208, the attenuation of at least one of the plurality of porosity standards 10 may be evaluated. For example, ultrasonic testing equipment may be used to measure the reduction in amplitude of an ultrasound beam as a function of porosity through the material of the porosity standard 10 (FIG. 2).

As shown at block 210, the attenuation measurement of the composite component may be compared to the attenuation measurement of at least one of the porosity standards 10.

As shown at block 212, the compared attenuation measurements may be used to validate the percent porosity of the composite component. For example, the attenuation measurement of the composite component may be compared to the attenuation measurement of a first porosity standard 10a (FIG. 2). If the attenuation measurement of the composite component is less than the attenuation measurement of the first porosity standard 10a, then the percent porosity of the composite component may be assumed to be no greater than the percent porosity of the first porosity standard 10a. If the attenuation measurement of the composite component is greater than the attenuation measurement of the first porosity standard 10a, then the percent porosity of the composite components may be assumed to be greater than the percent porosity of the first porosity standard 10a.

As an illustrative example, the acceptable percent porosity of the composite component may not exceed 4%. The attenuation measurement of at least one location of or across the composite component (e.g., manufactured composite part or composite repair) may be 7 decibel (dB). The attenuation measurement of a first porosity standard representing 0% porosity may be 2 dB. Since the attenuation measurement of the composite component is greater than the attenuation measurement of the 0% porosity standard, it may be assumed that the percent porosity of the composite component is greater than 0%. The attenuation measurement of a second porosity standard representing 8% porosity may be 13 dB. Since the attenuation measurement of the composite component is less than the attenuation measurement of the 8% porosity standard, it may be assumed that the percent porosity of the composite component is less than 8%. The attenuation measurement of a third porosity standard representing 4% porosity may be 6 dB. Since the attenuation measurement of the composite component is less than the attenuation measurement of the 4% porosity standard, it may be assumed that the percent porosity of the composite component is less than 4%.

Figure 7:
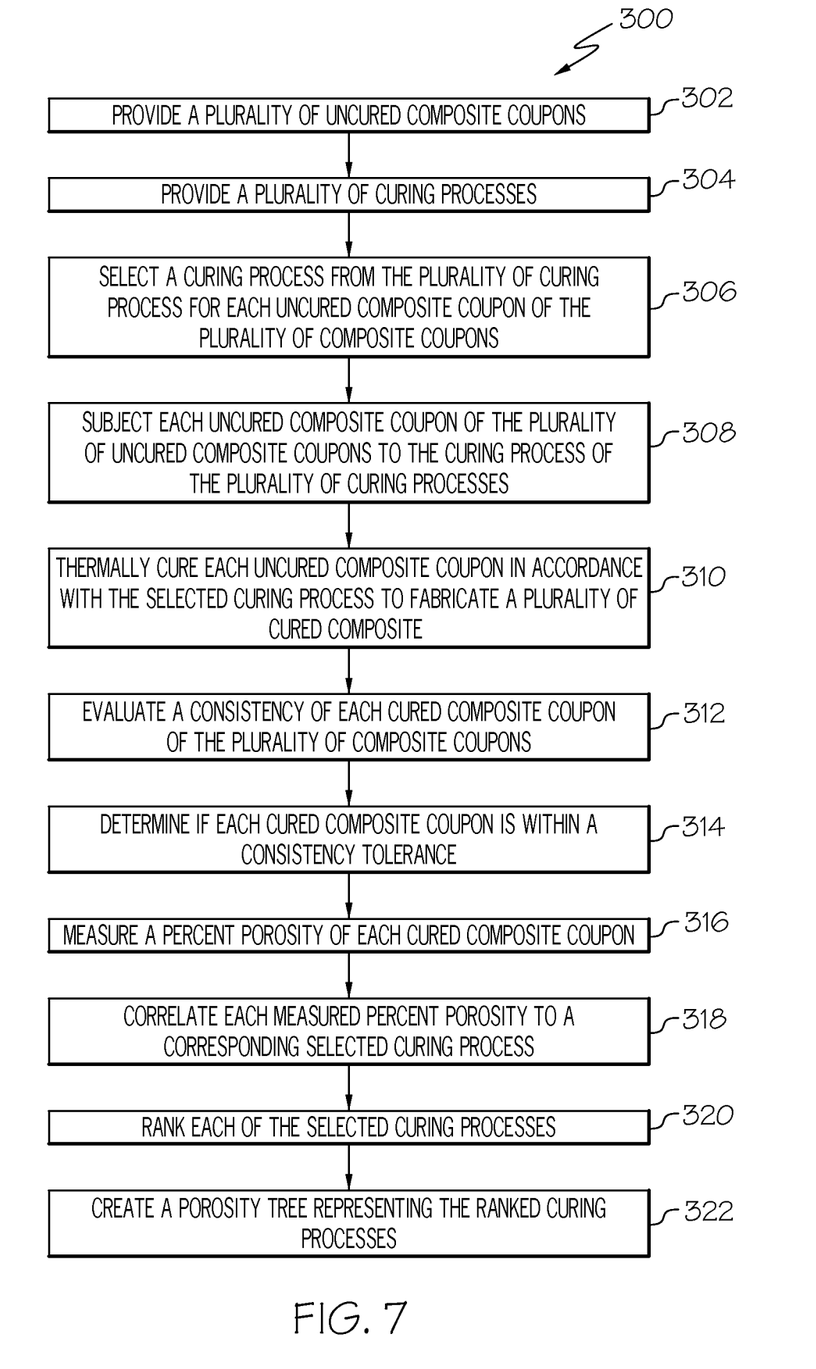
FIG. 7 is flow diagram of an aspect of the disclosed method for developing a percent porosity tree for selection of a plurality of curing processes.
Figure 8:
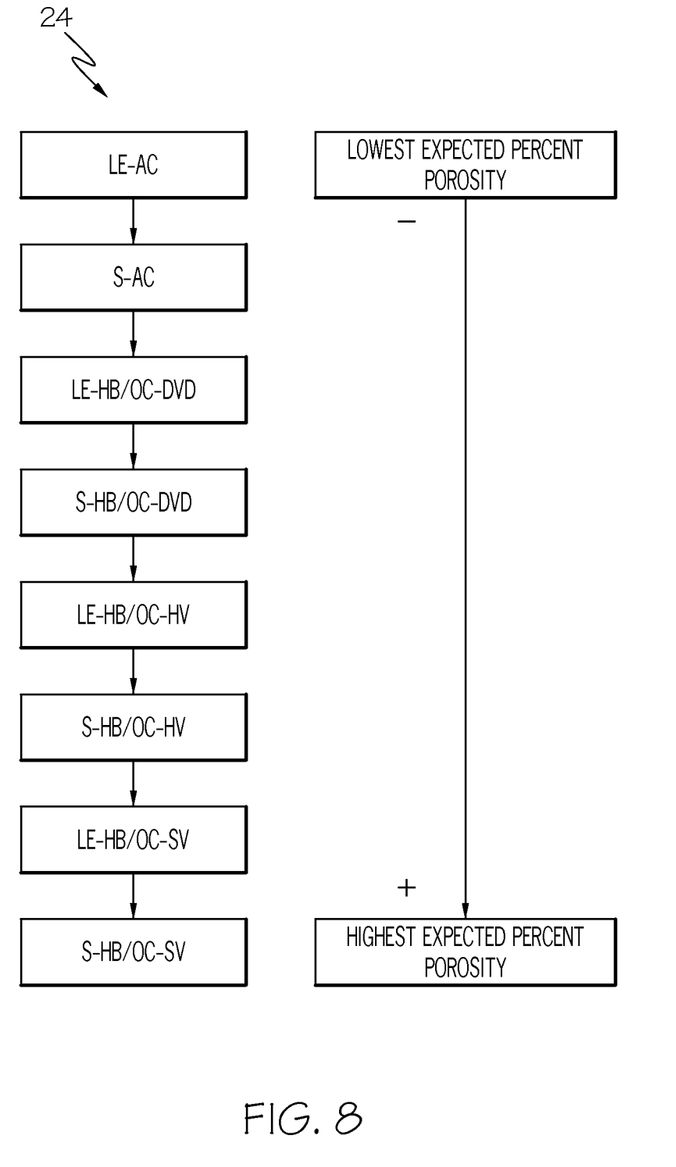
FIG. 8 is an illustration of an example aspect of the disclosed percent porosity tree.

Referring to FIGS. 7 and 8, also disclosed is a method, generally designated 300, for developing a percent porosity tree 24 (FIG. 8) for selection of a plurality of curing processes in accordance with the method 100 (FIG. 1) for fabricating porosity standards. The disclosed method 300 may be used to predict a relative porosity of a cured composite coupon 16 when subjected to the selected curing process 14 (FIG. 2).

It can be appreciated that when fabricating a plurality of porosity standards 10, utilization of every type of curing process 14 (FIG. 2) may be unavailable or undesirable. Therefore, it may be beneficial to develop a tree 20 (e.g., chart) that may rank a plurality of selected curing processes 14 from the curing process 14 expected to produce the lowest percent porosity in a given cured composite material 20 to the curing process 14 expected to produce the highest percent porosity in a given cured composite material 20.

As shown at block 302, the method 300 may include the step of providing a plurality of uncured composite coupons 12 (FIG. 2), similar to that described above in the method step shown at block 102 of FIG. 1. As shown at block 304, a plurality of curing processes 14 (FIG. 2) may be provided, similar to that described above in the method step shown at block 104 of FIG. 1. As shown at block 306, a curing process 14a-14f of the plurality of curing processes 14 may be selected for each uncured composite coupon 12a-12f of the plurality of uncured composite coupons 12, similar to that described above in the method step shown at block 106 of FIG. 1.

As shown at block 308, each uncured composite coupon 12 of the plurality of uncured composite coupons 12 may be subjected to the selected curing process 14 of the plurality of curing processes 14 (FIG. 2). As shown at block 310, the plurality of composite coupons 12 may be thermally cured to form a plurality of cured composites 16 (FIG. 2) similar to that described above in the method step shown at block 110 of FIG. 1.

As shown at block 312, the consistency of each cured composite coupon 16a-16f (FIG. 2) of the plurality of cured composite coupons 16 may be evaluated, similar to that described above in the method step shown at block 112 of FIG. 1. As shown at block 314, upon validation of a consistent attenuation throughout the cured composite coupon 16, a determination may be made whether or not the cured composite coupon 16 meets any required minimum variation standards for use as a porosity reference standard 10 (FIG. 2), similar to that described above in the method step shown at block 114 of FIG. 1. As shown at block 316, the volumetric percent porosity in each validated cured composite coupon 16a-16f of the plurality of cured composite coupons 16 (FIG. 2) may be measured, similar to that described above in the method step shown at block 116 of FIG. 1.

As shown at block 318, the plurality of curing processes 14 and the measured percent porosities of the plurality of cured composite coupons 16 may be correlated such that each curing process 14a-14f may be identified by a corresponding measured percent porosity of each cured composite coupon 16a-16f subjected to that curing process 14.

As shown at block 320, the method 300 may include the step of ranking the each curing process 14a-14f (FIG. 2) of the plurality of curing processes 14 based on the measured percent porosity of the cured composite coupons 16 achieved through the associated curing process 14a-14f. The plurality of curing processes 14 may be ranked from the curing process 14 that achieves the lowest percent porosity in the selected composite material 20 (FIG. 3) (e.g., cured composite coupon) to the curing process 14 that achieved the highest percent porosity in the selected composite material 20 (e.g., cured composite coupon).

As shown at block 322, a porosity tree 24 (FIG. 8) may be created based upon the plurality of ranked curing processes 14. The number of curing processes 14 associated with the porosity tree 24 may depend upon the number of curing processes 14 selected in accordance with the method step shown at block 304. The porosity tree 24 provides a reference chart for the selection of certain curing processes 14 in accordance with the method step shown at block 104 of FIG. 1.

Referring to FIG. 8, illustrating a non-limiting example of the disclosed porosity tree 24 for a composite material 20 created in accordance with the method 300 (FIG. 7). The porosity tree 24 may represent eight curing processes 14 (FIG. 2) selected in accordance with the method step shown at block 304 of FIG. 7.

As illustrated, a composite material 20 (FIG. 3) subjected to a low exothermic autoclave curing process ("LE-AC") may be expected to have a lowest percent porosity relative to other selectable curing processes 14 of the plurality of curing processes 14.

A composite material subjected to a standard autoclave curing process ("S-AC") may be expected to have a percent porosity greater than that achieved through the low exothermic autoclave curing process and a lower percent porosity relative to other selectable curing processes 14 of the plurality of curing processes 14.

A composite material subjected to a low exothermic oven curing or heat blanket curing process under double vacuum debulk ("LE-OC/HB-DVD") may be expected to have a percent porosity greater than that achieved through the low exothermic autoclave curing process and the standard autoclave curing process and a lower percent porosity relative to other selectable curing processes 14 of the plurality of curing processes 14.

A composite material subjected to a standard oven curing or heat blanket curing process under double vacuum debulk ("S-OC/HB-DVD") may be expected to have a percent porosity greater than that achieved through the low exothermic autoclave curing process, the standard autoclave curing process, and the low exothermic oven curing or heat blanket curing process under double vacuum debulk and a lower percent porosity relative to other selectable curing processes 14 of the plurality of curing processes 14.

A composite material subjected to a low exothermic oven curing or heat blanket curing process under high vacuum ("LE-OC/HB-HV") may be expected to have a percent porosity greater than that achieved through the low exothermic autoclave curing process, the standard autoclave curing process, the low exothermic oven curing or heat blanket curing process under double vacuum debulk, and the standard oven curing or heat blanket curing process under double vacuum debulk and a lower percent porosity relative to other selectable curing processes 14 of the plurality of curing processes 14.

A composite material subjected to a standard oven curing or heat blanket curing process under high vacuum ("S-OC/HB-HV") may be expected to have a percent porosity greater than that achieved through the low exothermic autoclave curing process, the standard autoclave curing process, the low exothermic oven curing or heat blanket curing process under double vacuum debulk, the standard oven curing or heat blanket curing process under double vacuum debulk, and the low exothermic oven curing or heat blanket curing process under high vacuum and a lower percent porosity relative to other selectable curing processes 14 of the plurality of curing processes 14.

A composite material subjected to a low exothermic oven curing or heat blanket curing process under standard vacuum ("LE-OC/HB-SV") may be expected to have a percent porosity greater than that achieved through the low exothermic autoclave curing process, the standard autoclave curing process, the low exothermic oven curing or heat blanket curing process under double vacuum debulk, the standard oven curing or heat blanket curing process under double vacuum debulk, the low exothermic oven curing or heat blanket curing process under high vacuum, and the standard oven curing or heat blanket curing process under high vacuum and a lower percent porosity relative to other selectable curing processes 14 of the plurality of curing processes 14.

One skilled in the art will appreciate that increasing the number of repetitive ply-by-ply compactions of the uncured composite coupon 12 may provide for a greater reduction of volumetric percent porosity in the cured composite coupon 16 and, thus, the reference porosity standard 10.

A composite material subjected to a standard oven curing or heat blanket curing process under standard vacuum ("S-OC/HB-SV") may be expected to have a percent porosity greater than that achieved through the low exothermic autoclave curing process, the standard autoclave curing process, the low exothermic oven curing or heat blanket curing process under double vacuum debulk, the standard oven curing or heat blanket curing process under double vacuum debulk, the low exothermic oven curing or heat blanket curing process under high vacuum, the standard oven curing or heat blanket curing process under high vacuum, and the low exothermic oven curing or heat blanket curing process under standard vacuum and a lower percent porosity relative to other selectable curing processes 14 of the plurality of curing processes 14.

Referring again to FIG. 7, as shown at block 322, the method 300 may include the step of selecting a plurality of curing processes 14 (FIG. 2) from the porosity tree 24 (FIG. 8) for use in fabricating a plurality of porosity standards 10 (FIG. 2) in accordance with the method 100 shown in FIG. 1. For example, the step of selecting a plurality of curing processes 14 as shown at block 104 of FIG. 1 may be achieved by using the porosity tree 24 created through the process described in accordance with the method 300.

In an example implementation of the method 100 shown in FIG. 1, the curing process 14 expected to provide the lowest percent porosity, the curing process 14 expected to provide the highest percent porosity, and the curing process 14 expected to provide a percent porosity between the lowest percent porosity and the highest percent porosity may be selected, in accordance with the method step shown at block 104 of FIG. 1. A plurality of porosity standards 10 (FIG. 2) may be fabricated in accordance to the method steps shown at blocks 106-116. The plurality of reference porosity standards 10 may represent a range of percent porosities for use in accordance with the method 200 shown in FIG. 6.

If the plurality of porosity standards 10 represents a range of percent porosities required for validating a percent porosity of a composite component, then the method 100 described in FIG. 1 may be complete.

For example, a first curing process 14a expected to provide the lowest percent porosity (e.g., low exothermic autoclave curing process) may achieve a porosity of 0.5%. A second curing process 14b expected to provide the highest percent porosity (e.g., standard oven curing process under standard vacuum) may achieve a porosity of 4%. A third curing process 14c expected to provide a percent porosity between the lowest percent porosity and the highest percent porosity (e.g., low exothermic heat blanket curing process under high vacuum) may achieve a porosity of 1.5%. Thus the method 100 may provide a set of three porosity standards 10 representing three percent porosities including 0.5%, 1.5%, and 4%.

If additional porosity standards 10 representing percent porosities not represented in the initial group (e.g., set) of fabricated porosity standards 10 are needed, then at least one additional curing process 14 (FIG. 2) may be selected from the porosity tree 24 (FIG. 8).

For example, a fourth curing process 14d expected to provide a percent porosity between the second curing process 14b and the third curing process 14c may be selected, in accordance with the method step shown at block 104 of FIG. 1. The fourth curing process 14d expected to provide a percent porosity between 1.5% and 4% (e.g., low exothermic heat blanket curing process under standard vacuum) may achieve a porosity of 2%. Thus the method 100 may provide a set of four porosity standards 10 representing four percent porosities including 0.5%, 1.5%, 2%, and 4%.

This process may be repeated iteratively until a complete set of reference porosity standards 10 is fabricated representing discrete percent porosities within a range of percent porosities required for validation of the percent porosity of a composite component having substantially the same composite material, such as the same material grade, class and type and the number of plies.

Figure 9:
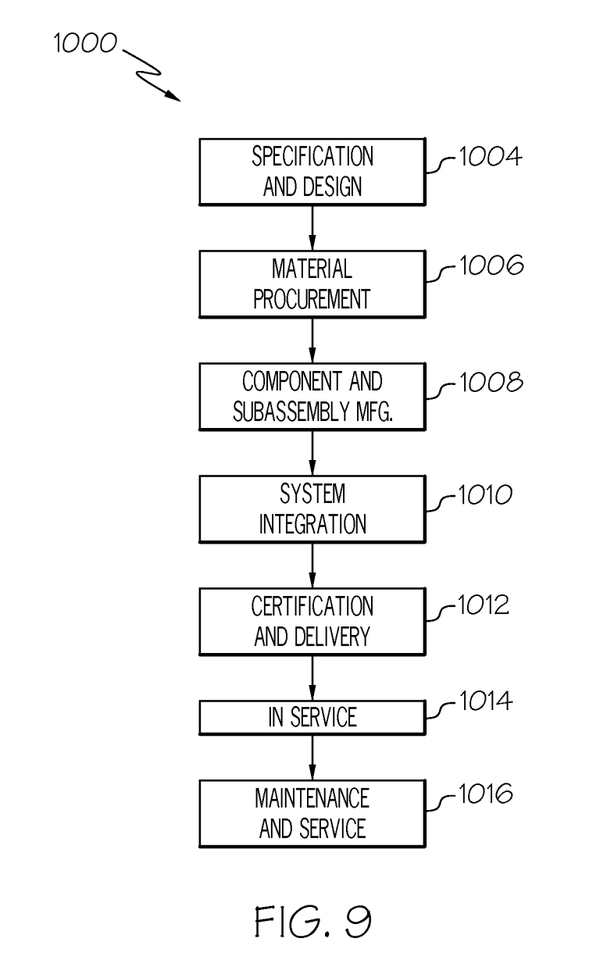
FIG. 9 is a flow diagram of aircraft production and service methodology.
Figure 10:
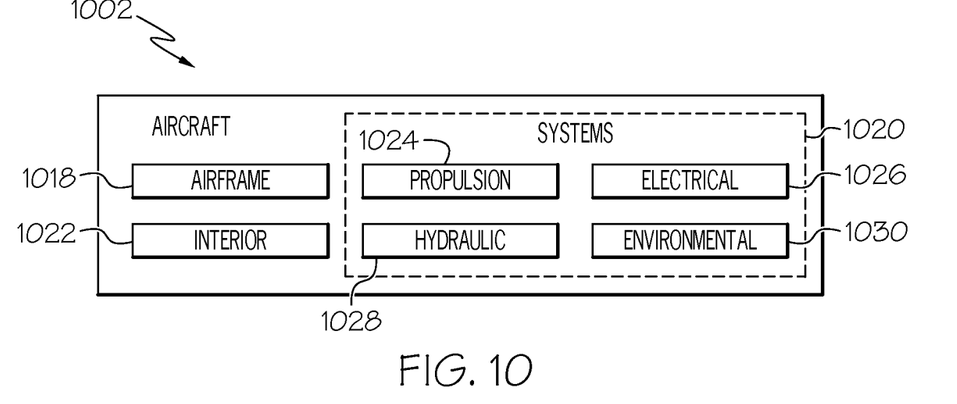
FIG. 10 is a block diagram of an aircraft.

Examples of the disclosure may be described in the context of an aircraft manufacturing and service method 1000, as shown in FIG. 9, and an aircraft 1002, as shown in FIG. 10. During pre-production, example method 1000 may include specification and design 1004 of the aircraft 1002 and material procurement 1006, both of which may employ the disclosed porosity standards. During production, component and subassembly manufacturing 1008 and system integration 1010 of the aircraft 1002 takes place. The disclosed porosity standards may be used during component and subassembly manufacturing 1008 and/or during system integration 1010. Thereafter, the aircraft 1002 may go through certification and delivery 1012 in order to be placed in service 1014. While in service by a customer, the aircraft 1002 is scheduled for routine maintenance and service 1016, which may also include modification, reconfiguration, refurbishment and the like using the disclosed porosity standards.

Each of the processes of method 1000 may be performed or carried out by a system integrator, a third party, and/or an operator (e.g., a customer). For the purposes of this description, a system integrator may include without limitation any number of aircraft manufacturers and major-system subcontractors; a third party may include without limitation any number of venders, subcontractors, and suppliers; and an operator may be an airline, leasing company, military entity, service organization, and so on.

As shown in FIG. 10, the aircraft 1002 produced by example method 1000 may include an airframe 1018 with a plurality of systems 1020 and an interior 1022. Examples of high-level systems 1020 include one or more of a propulsion system 1024, an electrical system 1026, a hydraulic system 1028, and an environmental system 1030. Any number of other systems may be included. Although an aerospace example is shown, the principles of the disclosure may be applied to other industries, such as the automotive industry.

Apparatus and methods embodied herein may be employed during any one or more of the stages of the production and service method 1000. For example, components or subassemblies corresponding to production process 1008 may be fabricated or manufactured in a manner similar to components or subassemblies produced while the aircraft 1002 is in service. Also, one or more apparatus examples, method examples, or a combination thereof may be utilized during the production stages 1008 and 1010, for example, by substantially expediting assembly of or reducing the cost of an aircraft 1002. Similarly, one or more of apparatus examples, method examples, or a combination thereof may be utilized while the aircraft 1002 is in service, for example and without limitation, to maintenance and service 1016.

Accordingly, the disclosed method for fabricating reference porosity standards may provide a systematic and standardized approach to selecting a plurality of curing processes for the fabrication of a plurality of porosity standards having naturally occurring porosity for a given composite material. The ability to produce naturally occurring porosity may make the disclosed method desirable in the manufacturing of natural porosity standards. Additionally, the nature of the disclosed process, including its tailorability and repeatability, may enable the production of multiple porosity reference standards having substantially equivalent porosity properties to allow nondestructive inspection of porous composite parts. The disclosed method may become the foundation for the development of natural porosity standards to calibrate and characterize ultrasonic testing equipment and may replace current composite reference standards, which attempt to artificially simulate porosity.

Although various aspects of the disclosed method for fabricating porosity standards have been shown and described, modifications may occur to those skilled in the art upon reading the specification. The present application includes such modifications and is limited only by the scope of the claims.

What is claimed is:

1. A method for fabricating a composite porosity standard, said method comprising:
    selecting a curing process from a porosity tree of a plurality of curing processes ranked by a predicted percent porosity of a selected composite material expected to be obtained by each of said plurality of curing processes;
    curing an uncured composite coupon comprising said selected composite material in accordance with said curing process selected from said porosity tree to form a cured composite coupon having a percent porosity corresponding to said predicted percent porosity;
    measuring said percent porosity of said cured composite coupon; and
    correlating a measured percent porosity to said cured composite coupon to form said composite porosity standard.

2. The method of claim 1 wherein said uncured composite coupon includes a length dimension, a width dimension and a thickness dimension optimized to achieve a consistent porosity throughout said cured composite coupon, and wherein said method further comprises validating a porosity consistency of said cured composite coupon by comparing said porosity consistency to a predetermined porosity consistency tolerance.

3. The method of claim 2 wherein said length dimension is no greater than twelve inches and said width dimension is no greater than twelve inches.

4. The method of claim 2 wherein said length dimension is no greater than twelve inches and said width dimension is no greater than six inches.

5. A method for fabricating composite porosity standards, said method comprising:
    providing a plurality of uncured composite coupons, each uncured composite coupon of said plurality of uncured composite coupons comprising a selected composite material;
    providing a porosity tree of a plurality of curing processes ranked by predicted percent porosities of said selected composite material expected to be obtained by each curing process of said plurality of curing processes;
    selecting particular curing processes from said plurality of curing processes to be associated with said each uncured composite coupon to obtain an expected percent porosity;
    curing said each uncured composite coupon in accordance with an associated particular curing process to form a plurality of cured composite coupons having percent porosities corresponding to said predicted percent porosities;
    measuring a percent porosity of each cured composite coupon of said plurality of cured composite coupons; and
    correlating a measured percent porosity to a corresponding cured composite coupon of said plurality of cured composite coupons to form a plurality of composite porosity standards representing a range of percent porosities.

6. The method of claim 5 wherein said each uncured composite coupon includes a length dimension, a width dimension and a thickness dimension optimized to promote consistent out-gassing of moisture within said selected composite material from edges of said uncured composite coupon during said associated particular curing process to achieve a consistent porosity throughout said each cured composite coupon.

7. The method of claim 6 further comprising evaluating a porosity consistency throughout said each cured composite coupon by comparing said porosity consistency to a predetermined porosity consistency tolerance.

8. The method of claim 7 wherein said porosity consistency of said each cured composite coupon is measured by ultrasonic testing.

9. The method of claim 6 wherein said said length dimension is no greater than twelve inches and said width dimension is no greater than twelve inches.

10. The method of claim 6 wherein said length dimension is no greater than twelve inches and said width dimension is no greater than six inches.

11. The method of claim 5 wherein said selected curing process comprises at least one of a low exothermic autoclave curing process, a standard autoclave curing process, a low exothermic heat blanket curing process under double vacuum debulk, a low exothermic oven curing process under double vacuum debulk, a standard heat blanket curing process under double vacuum debulk, a standard oven curing process under double vacuum debulk, a low exothermic heat blanket curing process under high vacuum, a low exothermic oven curing process under high vacuum, a standard heat blanket curing process under high vacuum, a standard oven curing process under high vacuum, a low exothermic heat blanket curing process under standard vacuum, a low exothermic oven curing process under standard vacuum, a standard heat blanket curing process under standard vacuum, and a standard oven curing process under standard vacuum.

12. The method of claim 5 further comprising generating said porosity tree comprising:
    providing said plurality of curing processes;
    providing a plurality of uncured composite test coupons, each uncured composite test coupon of said plurality of uncured composite test coupons comprising a test composite material;
    curing said each uncured composite material in accordance with an associated one of said plurality of curing processes to form a plurality of cured composite test coupons;
    measuring a test percent porosity of each cured composite test coupon of said plurality of cured composite test coupons;
    correlating each measured test percent porosity with said associated one of said plurality of curing processes;
    ranking said plurality of curing processes from a lowest test percent porosity to a highest test percent porosity to generate said porosity tree,
    wherein said selected material is the same as said test composite material.

13. The method of claim 12 wherein said each uncured composite test coupon includes a length dimension, a width dimension and a thickness dimension optimized to promote consistent out-gassing of moisture within said test composite material from edges of said uncured composite test coupon during said associated one of said plurality of curing processes to achieve a consistent porosity throughout said each cured composite test coupon, and wherein said method further comprises evaluating a porosity consistency of said each cured composite test coupon by comparing said porosity consistency to a predetermined porosity consistency tolerance.

14. The method of claim 5 wherein said measured percent porosity of said each cured composite coupon is measured by imaging analysis.

15. The method of claim 14 wherein said imaging analysis comprises digital image processing.

16. The method of claim 14 wherein said imaging analysis comprises computed tomography.

17. The method of claim 5 further comprising providing a composite component comprising a component composite material, wherein said selected composite material is substantially the same as said component composite material.

18. The method of claim 17 further comprising:
evaluating an attenuation of said composite component by ultrasonic testing;
evaluating an attenuation of at least one composite porosity standard of said plurality of composite porosity standards by said ultrasonic testing;
comparing attenuation measurements of said composite component to attenuation measurements of said at least one composite porosity standard; and
validating a percent porosity of said composite component based on a comparison of said attenuation measurements of said composite component and said attenuation measurements of said at least one porosity standard.

19. The method of claim 5 wherein said selected composite material comprises a composite lay-up comprising at least two plies.

20. The method of claim 5 wherein said selected composite material comprises a prepreg material.

21. The method of claim 5 wherein said selected composite material comprises a wet lay-up material.

22. A composite porosity reference standard comprising:
a cured composite coupon comprising a selected composite material and having a percent porosity and a consistent porosity throughout, said percent porosity corresponding to a predicted percent porosity of said selected composite material obtained by a particular curing process selected from a porosity tree of a plurality of curing processes ranked by predicted percent porosities; and
a measured percent porosity of said cured composite coupon identifying said composite porosity standard.

23. The standard of claim 22 wherein said selected composite material comprises a prepreg material.

24. The standard of claim 22 wherein said selected composite material comprises a wet lay-up material.

* * * * *